United States Patent
Enomoto

(10) Patent No.: US 9,398,852 B2
(45) Date of Patent: Jul. 26, 2016

(54) MEDICAL TELEMETRY SYSTEM AND MEDICAL TELEMETER

(75) Inventor: Yoshinori Enomoto, Tokyo (JP)

(73) Assignee: NIHON KOHDEN CORPORATION, Tokyo (JP)

(*) Notice: Subject to any disclaimer, the term of this patent is extended or adjusted under 35 U.S.C. 154(b) by 1218 days.

(21) Appl. No.: 13/228,586

(22) Filed: Sep. 9, 2011

(65) Prior Publication Data

US 2012/0065477 A1    Mar. 15, 2012

(30) Foreign Application Priority Data

Sep. 10, 2010  (JP) .................................. 2010-203132
May 17, 2011  (JP) .................................. 2011-110381

(51) Int. Cl.
*A61B 5/02* (2006.01)
*G01D 5/00* (2006.01)
*H04B 1/405* (2015.01)
*H04W 72/00* (2009.01)
*A61B 5/00* (2006.01)
*G06F 19/00* (2011.01)
*A61B 5/021* (2006.01)
*A61B 5/024* (2006.01)
*A61B 5/08* (2006.01)

(52) U.S. Cl.
CPC ............... *A61B 5/0006* (2013.01); *A61B 5/002* (2013.01); *G06F 19/3418* (2013.01); *A61B 5/021* (2013.01); *A61B 5/02438* (2013.01); *A61B 5/0816* (2013.01); *A61B 2562/08* (2013.01)

(58) Field of Classification Search
CPC  G06F 19/3418; A61B 5/0002; A61B 5/1113; G08B 13/14; H04J 3/00; H04W 72/04
USPC ........................................ 340/539.12, 539.1
See application file for complete search history.

(56) References Cited

U.S. PATENT DOCUMENTS

| | | | |
|---|---|---|---|
| 4,974,185 A | 11/1990 | Ohno et al. | |
| 5,036,869 A | 8/1991 | Inahara | |
| 5,690,119 A | 11/1997 | Rytky et al. | |
| 6,340,932 B1* | 1/2002 | Rodgers et al. | 340/572.7 |
| 2004/0106854 A1 | 6/2004 | Muraki | |
| 2004/0193453 A1* | 9/2004 | Butterfield et al. | 705/2 |

(Continued)

FOREIGN PATENT DOCUMENTS

| | | |
|---|---|---|
| CN | 1875878 A | 12/2006 |
| CN | 101161195 A | 4/2008 |

(Continued)

OTHER PUBLICATIONS

Office Action dated Mar. 28, 2014 issued by the Japanese Patent Office in counterpart Japanese Patent Application No. 2011-110381.

(Continued)

*Primary Examiner* — Jennifer Mehmood
*Assistant Examiner* — Pameshanand Mahase
(74) *Attorney, Agent, or Firm* — Sughrue Mion, PLLC

(57) ABSTRACT

A medical telemetry system include: a transmitter which transmits a first signal; a first medical telemeter which transmits a second signal including biological information of a patient, the first medical telemeter which receives the first signal and which performs an operation corresponding to information included in the first signal; and a monitor apparatus which receives the second signal.

21 Claims, 5 Drawing Sheets

(56) References Cited

U.S. PATENT DOCUMENTS

| | | |
|---|---|---|
| 2005/0027197 A1 | 2/2005 | Segawa et al. |
| 2005/0119582 A1 | 6/2005 | Matsumura et al. |
| 2006/0247736 A1 | 11/2006 | Roberts |
| 2006/0250259 A1 | 11/2006 | Izumi |
| 2006/0279427 A1 | 12/2006 | Becker et al. |
| 2007/0267475 A1* | 11/2007 | Hoglund et al. ............. 235/375 |
| 2008/0218376 A1* | 9/2008 | Dicks et al. ............. 340/870.01 |
| 2009/0040044 A1 | 2/2009 | Chiao et al. |
| 2009/0105567 A1* | 4/2009 | Smith et al. .................... 600/323 |
| 2009/0184842 A1* | 7/2009 | Baldus et al. ............ 340/870.07 |
| 2009/0231124 A1* | 9/2009 | Klabunde et al. ........ 340/539.12 |
| 2009/0233615 A1* | 9/2009 | Schmitt .............. H04W 72/005 455/452.1 |

FOREIGN PATENT DOCUMENTS

| | | |
|---|---|---|
| CN | 101287405 A | 10/2008 |
| CN | 101342092 A | 1/2009 |
| EP | 0 747 003 A1 | 12/1996 |
| JP | 62-261334 A | 11/1987 |
| JP | 1-248816 A | 10/1989 |
| JP | 5-161611 A | 6/1993 |
| JP | 10-248816 A | 9/1998 |
| JP | 2001-314378 A | 11/2001 |
| JP | 2002-219109 A | 8/2002 |
| JP | 2005-344 A | 1/2005 |
| JP | 2005-177342 A | 7/2005 |
| JP | 2008-539004 A | 11/2008 |
| JP | 2010-69193 A | 4/2010 |

OTHER PUBLICATIONS

Final rejection dated Nov. 4, 2014 issued by the Japanese Patent Office in counterpart Japanese Patent Application No. 2011-110381.
Office Action dated Jun. 9, 2014 issued by the State Intellectual Property Office of the People's Republic of China in counterpart Chinese Patent Application No. 201110272268.7.
European Search Report dated Apr. 14, 2015 issued by the European Patent Office in counterpart European Application No. 11180553.7.

* cited by examiner

MEDICAL TELEMETRY SYSTEM AND MEDICAL TELEMETER

BACKGROUND OF THE INVENTION

The present invention relates to a medical telemetry system and a medical telemeter, and particularly to a medical telemetry system and medical telemeter which are to be used in an inpatient ward of a hospital or the like, and which can time sequentially measure biological information such as the blood pressure and heart rate of a patient.

In an inpatient ward of a hospital or the like, a medical telemetry system has been used for monitoring a patient. As described in JP-A-5-161611, for example, a related-art medical telemetry system is configured by a transmitter which wirelessly transmits biological information (measurement data) obtained by performing measurements on a patient, and a receiver which displays and records the transmitted biological information.

Recently, a transmitter which is portable by a patient is in widespread use. Therefore, a patient can freely move in an inpatient ward while measurements of biological information such as the blood pressure and the heart rate are continued. The widespread use of such a portable transmitter causes a problem in that the location of a patient cannot be known. As a countermeasure against the problem, there is a related-art system, disclosed in JP-A-10-248816, which can roughly detect the current position of a patient.

In accordance with widespread use of such an above-described related-art portable transmitter, there arises a necessity that, when a doctor or a nurse wishes to call back a patient to a patient room, the doctor or the nurse must seek the patient in a ward of a hospital or page the patient over a loudspeaker. A method may be possible in which transmitters to be carried by patients are provided with functions of receiving different frequencies, respectively, and a signal is transmitted to the transmitter which is carried by the patient to be paged. However, the medical frequency band is limited, and it is difficult to set a large number of transmission channels for the paging function.

SUMMARY

According to the invention, there is provided a medical telemetry system comprising: a transmitter which transmits a first signal; a first medical telemeter which transmits a second signal including biological information of a patient, the first medical telemeter which receives the first signal and which performs an operation corresponding to information included in the first signal; and a monitor apparatus which receives the second signal.

The transmitter may transmit the first signal, which includes a first identification code for identifying the first medical telemeter. The first medical telemeter determines whether the first identification code is included in the received first signal or not, and when the first medical telemeter determines that the first identification code is included in the received first signal, the first medical telemeter may perform the operation corresponding to the information included in the first signal.

The medical telemetry system may further include a second medical telemeter distinct from the first medical telemeter.

The transmitter may add a first identification code for identifying the first medical telemeter to the first signal, which includes a command indicating the operation to be performed by the first medical telemeter, then transmit the first signal.

The transmitter may transmit the first signal through a single channel.

The transmitter may transmit the first signal, which includes a command indicating the operation to be performed by the first medical telemeter, and the operation includes at least one of outputting of a sound, outputting of light, vibrating of the first medical telemeter, starting or stopping of measurement of the biological information, starting or stopping of transmission of the second signal, registering of patient information into the first medical telemeter, and checking of the patient information registered in the first medical telemeter.

The transmitter may be a short-range device, and the first medical telemeter may be a wireless medical telemetry device.

The monitor apparatus may transmit a first identification code for identifying the first medical telemeter and a command indicating the operation to be performed by the first medical telemeter to the transmitter, and the transmitter may transmit the first signal, which includes the first identification code and the command that are transmitted by the monitor apparatus.

The medical telemetry system may further include an external medical apparatus which transmits a first identification code for identifying the first medical telemeter and a command indicating the operation to be performed by the first medical telemeter to the transmitter. The transmitter may transmit the first signal, which includes the first identification code and the command that are transmitted by the external medical apparatus.

The medical telemetry system may further include an external medical apparatus which transmits a command indicating the operation to be performed by the first medical telemeter to the transmitter. The transmitter may have a first identification code for identifying the first medical telemeter, and transmit the first signal, which includes the first identification code and the command that is transmitted by the external medical apparatus.

The command may be an operation instruction command for causing the first medical telemeter to transmit the second signal which includes biological information measured by the external medical apparatus or an alarm issued by the external medical apparatus.

The medical telemetry system may further include an antenna which receives the second signal. The transmitter and the antenna may be integrally provided.

The transmitter may be provided in the monitor apparatus.

The medical telemetry system may further include: a patient information storage portion which stores patient information for identifying a patient; and a patient information acquiring portion which acquires the patient information from the patient information storage portion. The patient information acquiring portion may transmit a first identification code for identifying the first medical telemeter and the acquired patient information, to the transmitter, and the transmitter may transmit the first signal, which includes the identification code that is transmitted by the patient information acquiring portion and a command.

The medical telemetry system may further include: a patient information storage portion which stores patient information for identifying a patient; and a patient information acquiring portion which acquires the patient information from the patient information storage portion. The patient information acquiring portion may transmit the acquired patient information to the transmitter, and the transmitter may have a first identification code for identifying the first medical telemeter and transmit the first signal, which includes the first identification code and the patient information that is transmitted by the patient information acquiring portion.

The first medical telemeter may issue an alarm, when the patient information included in the received first signal does not coincide with patient information registered in the first medical telemeter.

The first medical telemeter may transmit the second signal, which includes the patient information that is included in the received first signal, to the monitor apparatus, and the monitor apparatus may issue an alarm, when the patient information included in the received second signal does not coincide with patient information registered in the monitor apparatus.

The first medical telemeter may transmit the second signal, which includes the patient information that is included in the received first signal, to the monitor apparatus, and the monitor apparatus may transmit a command for issuing an alarm to the transmitter, when the patient information included in the received second signal does not coincide with patient information registered in the monitor apparatus, then the transmitter may transmit the first signal which includes the first identification code and the command.

According to the invention, there is also provided a medical telemeter comprising: a measuring function, adapted to be attached to a patient, of measuring biological information of the patient; a receiving function of receiving a signal which is transmitted by a transmitter and which includes an identification code for identifying a medical telemeter; a transmitting function of transmitting the biological information to an antenna; and an ID determining function of determining whether the received signal includes the identification code for identifying the medical telemeter or not, wherein the medical telemeter performs an operation, when the ID determining function determines that the identification code for identifying the medical telemeter is included in the signal.

DETAILED DESCRIPTION OF EMBODIMENTS

Hereinafter, the invention will be described with reference to embodiments of the invention. The following embodiments do not limit the scope of the present invention, and not all combinations of the features described in the embodiments are essential to the invention.

Figure 1:
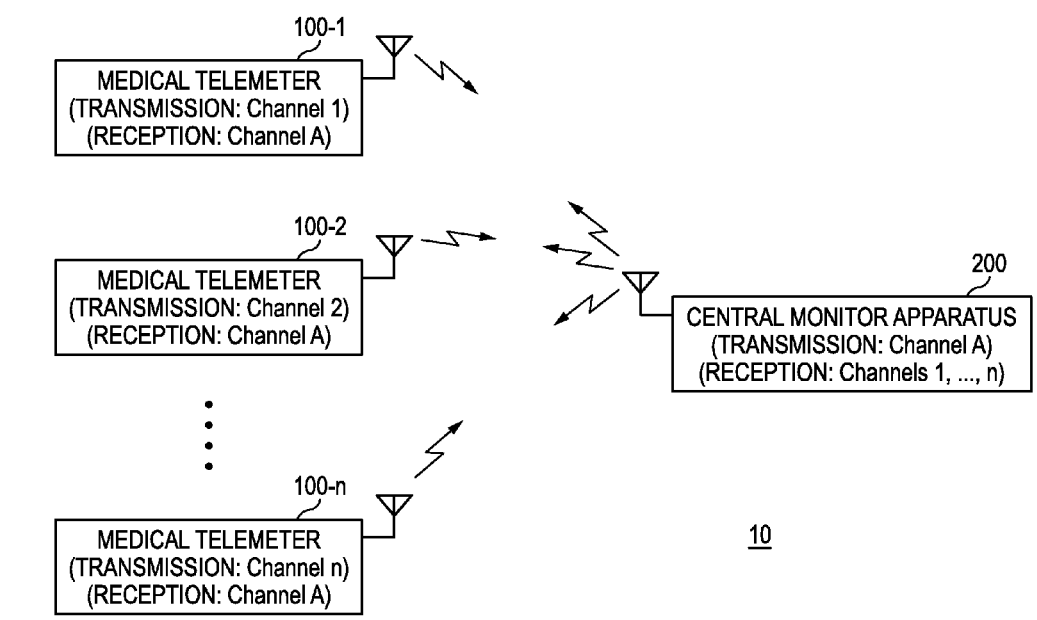
FIG. 1 is a schematic diagram of a medical telemetry system of a first embodiment of the invention.
Figure 2:
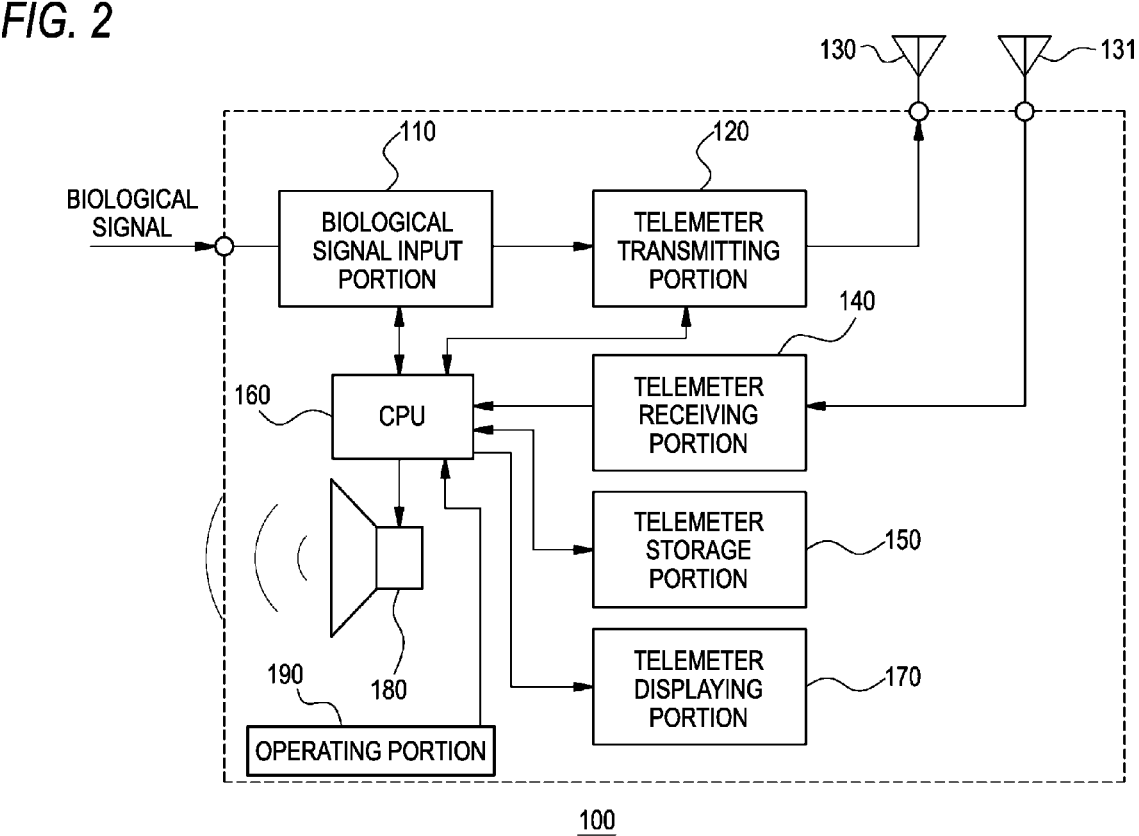
FIG. 2 is a block diagram showing a configuration example of a medical telemeter.
Figure 3:
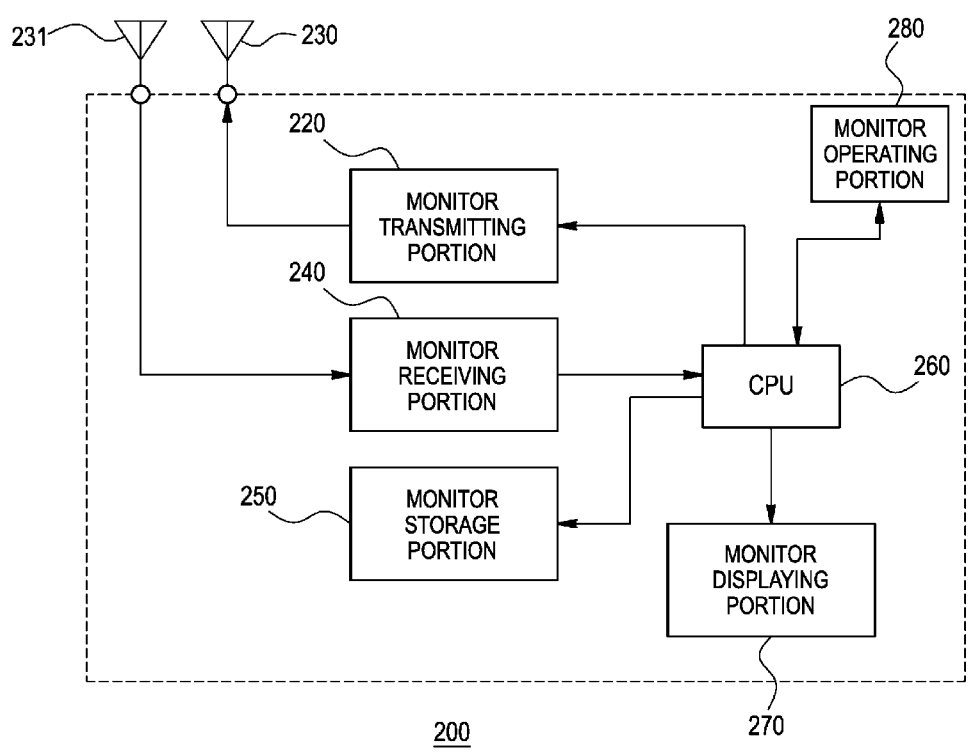
FIG. 3 is a block diagram showing a configuration example of a central monitor.

FIG. 1 is a schematic diagram of a medical telemetry system 10 of a first embodiment of the invention. FIG. 2 is a block diagram showing a configuration example of a medical telemeter 100, and FIG. 3 is a block diagram showing a configuration example of a central monitor 200.

The medical telemetry system 10 of the embodiment includes: a plurality of medical telemeters 100 (100-1, 100-2, ..., 100-n) each of which receives biological signals such as an electrocardiogram, respiration, blood pressure, and pulse wave of a patient from respective measuring apparatuses, which produces biological data including the received biological signals, patient information such as the name of the patient, and the like, and which transmits the biological data; and the central monitor 200 which receives the biological data transmitted from the medical telemeters 100 (100-1, 100-2, ..., 100-n), and which displays the biological data. Hereinafter, in the case where one of the plurality of medical telemeters 100-1, 100-2, ..., 100-n is not particularly specified, the medical telemeter is referred to as "medical telemeter 100" for the sake of convenience.

Each of the plurality of medical telemeters 100 is an apparatus having a size and weight which allow, for example, the patient to carry or move together with the telemeter, and, as shown in FIG. 2, has: a biological signal input portion 110; a telemeter transmitting portion 120; a transmission antenna 130 which transmits the measured biological data to a medical antenna disposed in a hospital; a reception antenna 131 and telemeter receiving portion 140 which receive signals that are transmitted from transmitters (such as a beacon which transmits position information) disposed in the hospital and those (such as a monitor transmitting portion 220 and transmission antenna 230 which will be described later) disposed in a monitor apparatus such as the central monitor 200 which will be described later; a telemeter storage portion 150; a CPU 160; a telemeter displaying portion 170; an audio output portion 180; and an operating portion 190 to which the user applies operations.

The medical telemeter 100 of the embodiment separately includes the transmission antenna 130 and the reception antenna 131. Alternatively, the telemeter may have a single antenna which can perform both transmission and reception. For example, the operations which are to be applied to the operating portion 190 by the user include start and stop of measurements of biological signals, those of transmission of the measured biological signals, registration of patient information into each of the medical telemeters 100, and correction of registered patient information, but are not limited to them. Each of the transmitters may receive a signal which is supplied from an external apparatus such as a personal computer, or that which is transmitted from an external medical apparatus such as an artificial respirator, and transmits the signal as a first signal. Moreover, the transmitter itself may hold an identification code of a predetermined medical telemeter, add the identification code held by itself to the received signal, and then transmit the resulting signal as the first signal. Here, the first signal means a wireless signal which is to be transmitted from the transmitter to the medical telemeter.

The biological signal input portion 110 is electrically connected to electrodes or transducers which are attached to, for example, the patient, and receives biological signals such as an electrocardiogram, respiration, blood pressure, and pulse wave which are output from the electrodes or the transducers. Then, the biological signal input portion 110 applies signal processes such as noise filtering and amplification to the received biological signals, and then transmits the processed signals to the telemeter transmitting portion 120.

The telemeter transmitting portion 120 receives the biological signals from the biological signal input portion 110, and also the identification code from the CPU 160. The identification code is a unique code for identifying the medical telemeter 100 in which the telemeter transmitting portion 120 is disposed, from the other medical telemeters 100, such as the apparatus ID, model number, serial number, and MAC address of the medical telemeter 100. The identification code may include information such as a channel number corresponding to the transmission frequency in the case where the telemeter transmitting portion 120 performs a transmission operation. The telemeter transmitting portion 120 produces biological data including the received biological signals and the identification code, and transmits the biological data through the transmission antenna 130 at a transmission frequency corresponding to the channel number which is preset by the user of the medical telemeter 100. The telemeter transmitting portion 120 may be a wireless medical telemetry device and may be a device transmitting the biological data in Wireless Medical Telemetry Service (WMTS).

In the embodiment, the transmission channels set respectively in the plurality of medical telemeters 100-1, 100-2, . . . , 100-n are different from one another. More specifically, as shown in FIG. 1, the telemeter transmitting portion 120 disposed in the medical telemeter 100-1 is set to "Channel 1". Namely, the telemeter transmitting portion 120 disposed in the medical telemeter 100-1 transmits biological data at a transmission frequency corresponding to Channel 1. The telemeter transmitting portion 120 disposed in the medical telemeter 100-2 is set to "Channel 2". Namely, the telemeter transmitting portion 120 disposed in the medical telemeter 100-2 transmits biological data at a transmission frequency which is different from that corresponding to Channel 1, and which corresponds to Channel 2.

In the embodiment, the frequencies respectively corresponding to the transmission channels (Channel 1, Channel 2, . . . , Channel n) set in the medical telemeters 100-1, 100-2, . . . , 100-n are selected from a band ranging from 420 to 450 MHz.

The telemeter receiving portion 140 receives command data transmitted from the central monitor 200, through the reception antenna 131. The command data are an example of the first signal in the invention, and, as described later, include a command which is to be executed by the specific medical telemeter 100, and the identification code of the specific medical telemeter 100.

The medical telemeter 100 in the embodiment receives through the reception antenna 131, a signal (command data) transmitted from the transmitter which is configured in the central monitor 200 by a monitor transmitting portion 220 and transmission antenna 230 that will be described later. Alternatively, the medical telemeter 100 may receive through the reception antenna 131, a signal (command data) transmitted from at least one of a transmitter(s) which is placed in one or a plurality of places in the hospital. In this case, all the reception channels set in the plurality of medical telemeters 100-1, 100-2, . . . , 100-n are identical to one another.

More specifically, as shown in FIG. 1, all the telemeter receiving portions 140 disposed respectively in the plurality of medical telemeters 100-1, 100-2, . . . , 100-n are set to "Channel A". Namely, the telemeter receiving portions 140 disposed in all the medical telemeters 100 (100-1, 100-2, . . . , 100-n) receive the command data at a reception frequency corresponding to Channel A. Preferably, the reception frequency corresponding to Channel A is a frequency (in, for example, the specified low power radio frequency band) which is different from all the transmission frequencies corresponding to the transmission channels (Channel 1, Channel 2, . . . , Channel n) set in the plurality of medical telemeters 100-1, 100-2, . . . , 100-n. The transmission antenna 130 and the reception antenna 131 may be configured by a same antenna which can perform both transmission and reception.

In the embodiment, the frequency corresponding to the reception channel (Channel A) set in the medical telemeters 100-1, 100-2, . . . , 100-n is selected from a band ranging from 312.5 to 314.5 MHz. In the embodiment, namely, the telemeter receiving portion 140 can receive a signal in the band of the specified low power radio communication (antenna power: 250 µW). Alternatively, the telemeter receiving portion 140 may be switchable between the band of the specified low power radio communication and that of the weak radio communication (antenna power: 500 µV/m).

The telemeter storage portion 150 stores the identification code of the medical telemeter 100 in which the portion itself is disposed, various settings of the medical telemeter 100, patient information such as the name of the patient under measurement, and the like. The telemeter storage portion 150 also stores the biological signals produced by the biological signal input portion 110, the command data received by the telemeter receiving portions 140, and the like.

In the operating portion 190, an interface is disposed which enables the user to start or stop measurements of biological signals (for example, the non-invasive blood pressure, the SpO2, and the body temperature), and to start or stop transmission of measured biological data, and to register or correct the patient information registered into the medical telemeters 100. When operated by the user, the portion causes, through the CPU 160, the biological signal input portion 110 to start measurements of biological signals (for example, the non-invasive blood pressure, the SpO2, and the body temperature), the telemeter transmitting portion 120 to transmit the measured signals through the antenna 130, and received patient information to be stored in the telemeter storage portion 150 and to be displayed on the telemeter displaying portion 170.

The CPU 160 controls the portions of the medical telemeter 100, and reads the identification code stored in the telemeter storage portion 150 to output the code to the telemeter transmitting portion 120. Furthermore, the CPU 160 reads the command data which are received by the telemeter receiving portions 140 and stored in the telemeter storage portion 150, and determines whether or not the identification code included in the command data coincides with the identification code stored in the telemeter storage portion 150, i.e., that which identifies the medical telemeter 100 from the other medical telemeters 100.

Only when the identification code included in the command data coincides with that of the medical telemeter 100 stored in the telemeter storage portion 150, the CPU 160 outputs execution instructions for executing the contents of a command included in the command data. More specifically, in the case where the telemeter receiving portions 140 receives command data including the identification code of the medical telemeter 100 and a command for outputting an alarm, for example, the CPU 160 outputs execution instructions for outputting an alarm, to the audio output portion 180. As described above, the CPU 160 has not only the function of controlling the portions of the medical telemeter 100, but also the ID determining function of determining whether or not the identification code (ID) included in the command data received by the telemeter receiving portion 140 includes an identification code which coincides with that of itself.

The telemeter displaying portion 170 is a display screen such as an LCD or a CRT, and displays the values of various biological signals supplied to the medical telemeter 100 in which the portion itself is disposed, the waveform, and the like.

In the embodiment, the audio output portion 180 is a speaker which can emit an electronic sound or a message to the patient. When execution instructions for outputting an alarm is supplied from the CPU 160 as described above, the portion emits an electronic sound or message corresponding to the contents of the execution instructions and indicating, for example, that the patient is to be paged, and that the inspection time is to be informed to the patient. Although not illustrated, the medical telemeter may include an optical outputting portion which emits light by means LEDs or the like, a vibration outputting portion which vibrates the medical telemeter, and the like.

As described above, the same reception channel is set in the plurality of medical telemeters 100, and therefore the command data transmitted from the central monitor 200 are received by all the medical telemeters 100. In a medical telemeter 100 in which the identification code included in the command data does not coincide with that stored in the telemeter storage portion 150 disposed in the telemeter itself, however, the contents of a command included in the command data is not executed, and, only in a medical telemeter 100 in which the identification code included in the command data coincides with that of itself, the contents of a command such as outputting of a sound or starting of measurement of a biological signal are executed. Namely, the plurality of medical telemeters 100 included in the medical telemetry system 10 of the embodiment have a function of determining whether command data broadcasted from the central monitor 200 are executed or not.

As shown in FIG. 3, the central monitor 200 has: the transmission antenna 230; the monitor transmitting portion 220 which transmits command data through the transmission antenna 230; a reception antenna 231; a monitor receiving portion 240 which receives biological data transmitted from the medical telemeter 100, through the reception antenna 231; a monitor storage portion 250; a CPU 260; a monitor displaying portion 270; and a monitor operating portion 280. The biological data are an example of the second signal in the invention. The contents of the biological data are not particularly limited as far as the contents are information included in a wireless signal which is to be transmitted from a usual medical telemeter to a monitor apparatus, and may include, in addition to the biological signal, patient information such as a patient ID and the name of the patient, alarm information, and the measurement state (for example, the existence of interruption of measurement due to detachment of electrodes or temporary room leaving) of biological signals, or like information.

The central monitor 200 is an example of the monitor apparatus in the invention, and the monitor transmitting portion 220 and the transmission antenna 230 are an example of the transmitter which transmits the first signal in the invention. In the embodiment, the transmitter is disposed in the monitor apparatus. Alternatively, the transmitter may be disposed independently from the monitor apparatus. In the alternative, the monitor apparatus and the transmitter are connected to each other by a wire, or by wireless. In the embodiment, the central monitor 200 which receives biological data of a plurality of patients is exemplified. Alternatively, for example, the central monitor 200 may be a bedside monitor which receives biological data of one patient. In the embodiment, the central monitor 200 includes separately the transmission antenna 230 and the reception antenna 231. Alternatively, the central monitor may include a single antenna which can perform both transmission and reception.

The monitor transmitting portion 220 broadcast transmits command data which are produced by the CPU 260 as described later, to all the medical telemeters 100 through the transmission antenna 230 at a frequency corresponding to a preset transmission channel. In the embodiment, the monitor transmitting portion 220 transmits the command data at a frequency corresponding to above-mentioned Channel A. The command data may include only the identification code, or, together with the identification code, include commands for performing predetermined operations such as "outputting of a sound", "outputting of light", "vibrating of the medical telemeter", "starting or stopping of measurements of biological signals", "starting or stopping of transmission of biological data", "registering of patient information", and "checking of patient information". These operations may be caused to be performed, through the monitor operating portion 280 by the user. Here, "registering of patient information" means an operation of storing predetermined patient information into the telemeter storage portion 150, and "checking of patient information" means an operation of checking whether or not the patient information held in the telemeter storage portion 150 of a predetermined medical telemeter 100 coincides with predetermined patient information broadcast transmitted from the monitor transmitting portion 220.

The monitor receiving portion 240 receives biological data transmitted from the plurality of medical telemeters 100 (100-1, 100-2, . . . , 100-$n$). Namely, the monitor receiving portion 240 can receive the frequencies corresponding to all the channels of Channel 1, Channel 2, . . . , Channel n.

In FIG. 3, only one transmission antenna 230 which transmits the command data, and one reception antenna 231 which receives the biological data are shown. However, for example, these antennas, and a transmission/reception apparatus having the functions of the monitor transmitting portion 220 and the monitor receiving portion 240 may be disposed in one or a plurality of places in a ward of the hospital.

The monitor storage portion 250 stores the identification codes of the plurality of medical telemeters 100-1, 100-2, . . . , 100-$n$, the patient information measured by the medical telemeters 100, various settings of the central monitor 200, and the like. The monitor storage portion 250 also stores the biological data and patient information transmitted from the plurality of medical telemeters 100-1, 100-2, . . . , 100-$n$, the command data transmitted from the monitor transmitting portion 220, and the like.

The CPU 260 controls the portions of the central monitor 200, and reads the identification codes of the plurality of medical telemeters 100-1, 100-2, . . . , 100-$n$ stored in the monitor displaying portion 270. In the case where, in the identification codes included in the biological data transmitted from the plurality of medical telemeters 100-1, 100-2, . . . , 100-$n$, there is a code which does not coincide with the identification code read from the monitor displaying portion 270, or there are two or more identical identification codes, the CPU 260 determines that there is a possibility of cross talk or misidentification, and outputs execution instructions for displaying a warning message, to the monitor displaying portion 270.

Based on a preset program or a predetermined external input by the user through the operating portion 280, the CPU 260 produces command data including a command (predetermined operation) to be executed by a specific medical telemeter 100, and the identification code of the medical telemeter 100. Then, the CPU 260 outputs the produced command data to the monitor transmitting portion 220.

The monitor displaying portion 270 is a display screen such as an LCD or a CRT, and displays the values of biological signals included in the biological data transmitted from the plurality of medical telemeters 100-1, 100-2, . . . , 100-$n$, the waveform, and the like. The display method is not particularly limited. In the case where the monitor displaying portion 270 receives the execution instructions for displaying a warning message from the CPU 260, the portion may display a warning message corresponding the contents of the execution instructions, in place of the display of biological data.

As described above, according to the medical telemetry system 10 of the embodiment, simply by ensuring at least one channel (Channel A) in addition to a channel (Channel 1, Channel 2, . . . , Channel n) which is required for transmitting biological data to the central monitor 200, various commands can be executed by wireless communication while selecting the medical telemeter 100 of a specific patient, for example, the specific medical telemeter 100 is caused to output an alarm to page the patient. As an example of the monitor apparatus in the medical telemetry system 10 of the embodiment, the central monitor 200 has been exemplified. However, the monitor apparatus is not limited to this, and may be any apparatus which can receive biological signals from a medical telemeter, such as a bedside monitor or a portable terminal that is carried by a medical person.

Embodiments using the invention are not limited to the medical telemetry system 10 configured by the medical telemeters 100 and the central monitor 200. Hereinafter, other embodiments will be described. In the following embodiments, the configurations which are identical with those of the above-described medical telemetry system 10 are denoted by the same reference numerals, and their description will be omitted.

Figure 4:
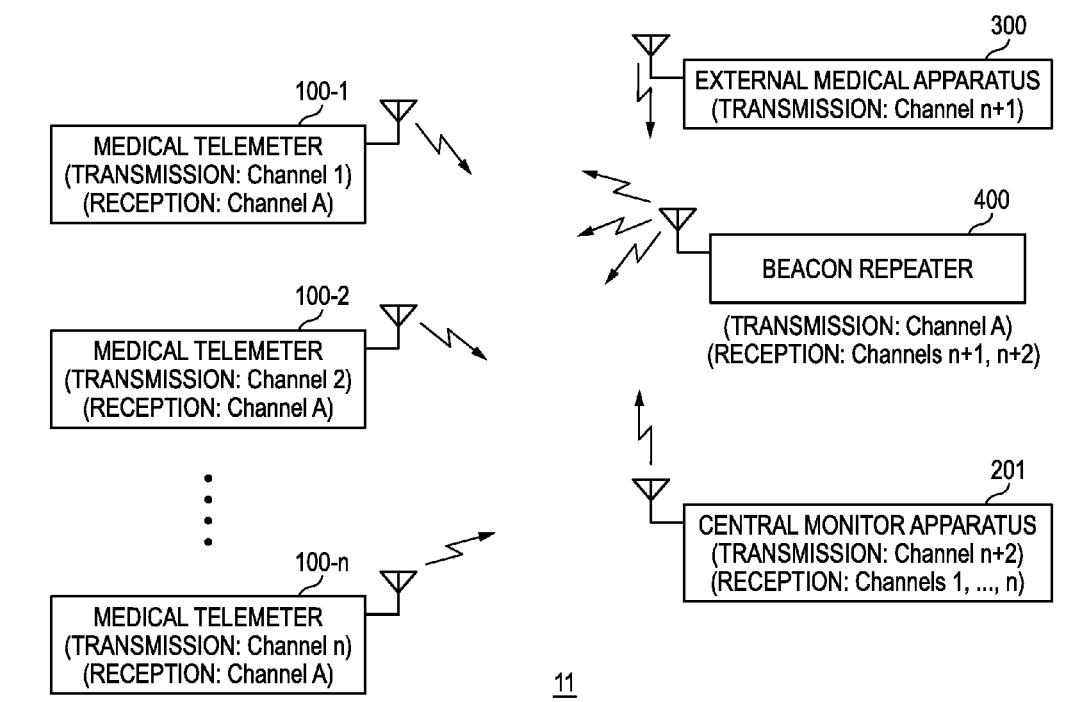
FIG. 4 is a schematic diagram of a medical telemetry system of a second embodiment of the invention.

FIG. 4 is a schematic diagram of a medical telemetry system 11 of a second embodiment of the invention. The medical telemetry system 11 of the embodiment is different from the above-described medical telemetry system 10 in that the system includes a central monitor 201 in place of the central monitor 200, and further includes an external medical apparatus 300 and a beacon repeater 400.

The external medical apparatus 300 may be a biological information measuring apparatus which can measure biological information (for example, the respiratory gas and the body temperature) of the patient, or a therapy apparatus which treats the patient, such as an artificial ventilator, or the like. In addition to a measuring portion (not shown) for measuring the biological information, the external medical apparatus 300 in the embodiment includes at least: a storage portion (not shown) for storing an identification code for identifying a specific medical telemeter 100-X (for example, the medical telemeter 100-1) from the other medical telemeters 100, and a command indicating contents of an operation which is to be executed by the specific medical telemeter 100-X; and a communicating portion (not shown) which can transmit the identification code and the command to the beacon repeater 400 through a predetermined transmission channel. The transmission channel which is used in the transmission of the identification code and the command from the external medical apparatus 300 to the beacon repeater 400 uses a frequency (in the embodiment, "Channel n+1") which is different from, for example, transmission frequencies of the transmission channels (Channel 1, Channel 2, . . . , Channel n) set in the plurality of medical telemeters 100-1, 100-2, . . . , 100-n in the medical radio frequency band.

For example, the command included in the signal which is transmitted from the external medical apparatus 300 to the beacon repeater 400 is an operation instruction command instructing that the biological information measured by the external medical apparatus 300 or information related to an alarm output from the external medical apparatus 300 is transmitted from the specific medical telemeter 100-X to the central monitor 201.

The beacon repeater 400 is an example of the transmitter in the invention, receives a signal which is transmitted from the external medical apparatus 300, and which includes the identification code and the command, and transmits the first signal including the identification code and the command, to the medical telemeter 100. The transmission channel of the beacon repeater 400 in the embodiment is set to Channel A which is identical with that of the central monitor 200 included in the medical telemetry system 10. Therefore, the transmission frequency of the beacon repeater 400 is a frequency in the specified low power radio frequency band which is different from all the transmission frequencies corresponding to the transmission channels (Channel 1, Channel 2, . . . , Channel n) set in the plurality of medical telemeters 100-1, 100-2, . . . , 100-n. The beacon repeater 400 is a short-range device.

The central monitor 201 is an example of the monitor apparatus in the invention, but, unlike the central monitor 200 included in the medical telemetry system 10, transmits command data including a command which is to be executed by the specific medical telemeter 100 and the identification code of the medical telemeter 100, through the beacon repeater 400 to the plurality of medical telemeters 100. As the frequency of the transmission channel which is used for transmitting the command data from the central monitor 201 to the beacon repeater 400, in order to prevent crosstalk with the first signal which is transmitted from the beacon repeater 400, and which is described later, a frequency (in the embodiment, set to "Channel n+2") is used which is different from, for example, the transmission frequencies of the transmission channels (Channel 1, Channel 2, . . . , Channel n) set in the plurality of medical telemeters 100-1, 100-2, . . . , 100-n in the medical radio frequency band, and the transmission frequency (Channel n+1) that is set in the external medical apparatus 300.

The second embodiment of the invention has shown the example in which the external medical apparatus 300 and the beacon repeater 400 communicate with each other by wireless. However, the external medical apparatus 300 is not required to be connected with the beacon repeater 400 by wireless communication, and may be connected therewith by wired communication. Alternatively, the external medical apparatus 300 and the beacon repeater 400 may be integrally formed. In the alternative, the beacon repeater 400 is not required to have a reception channel.

According to the above-described medical telemetry system 11, the biological information measured by the external medical apparatus 300 and the state of the external medical apparatus 300 such as an alarm issued therefrom can be transmitted through the beacon repeater 400 to the medical telemeter 100, and the biological information can be transmitted as the second signal from the medical telemeter 100 to the central monitor 201. When the system is configured by using the identification code for identifying the specific medical telemeter 100-X from the other medical telemeters 100 so that a plurality of external medical apparatuses 300 transmit biological information or the like through the beacon repeater 400 to different specific medical telemeters 100-X, respectively, biological information measured by the plurality of external medical apparatuses 300 can be centrally managed. This leads to improvement of the working efficiency of a medical person.

In the above-described medical telemetry system 11, the identification code is transmitted from the external medical apparatus 300. Alternatively, for example, the system may be configured so that the external medical apparatus 300 transmits only measured biological information and an alarm to the beacon repeater 400, and the beacon repeater 400 may hold the identification code of the specific medical telemeter 100-X. In this case, the beacon repeater 400 transmits an alarm transmitted from the external medical apparatus 300 and the identification code held by the beacon repeater 400, as the first signal (Channel A) to the medical telemeter 100. Then, the medical telemeter 100-X which receives the first signal including the identification code of itself from the beacon repeater 400 may be able to output, for example, the biological information measured by the external medical apparatus 300, and the contents of the alarm by means of displaying on the monitor displaying portion 270, printing, or the like, and further transmit as the second signal to the central monitor 201.

Figure 5:
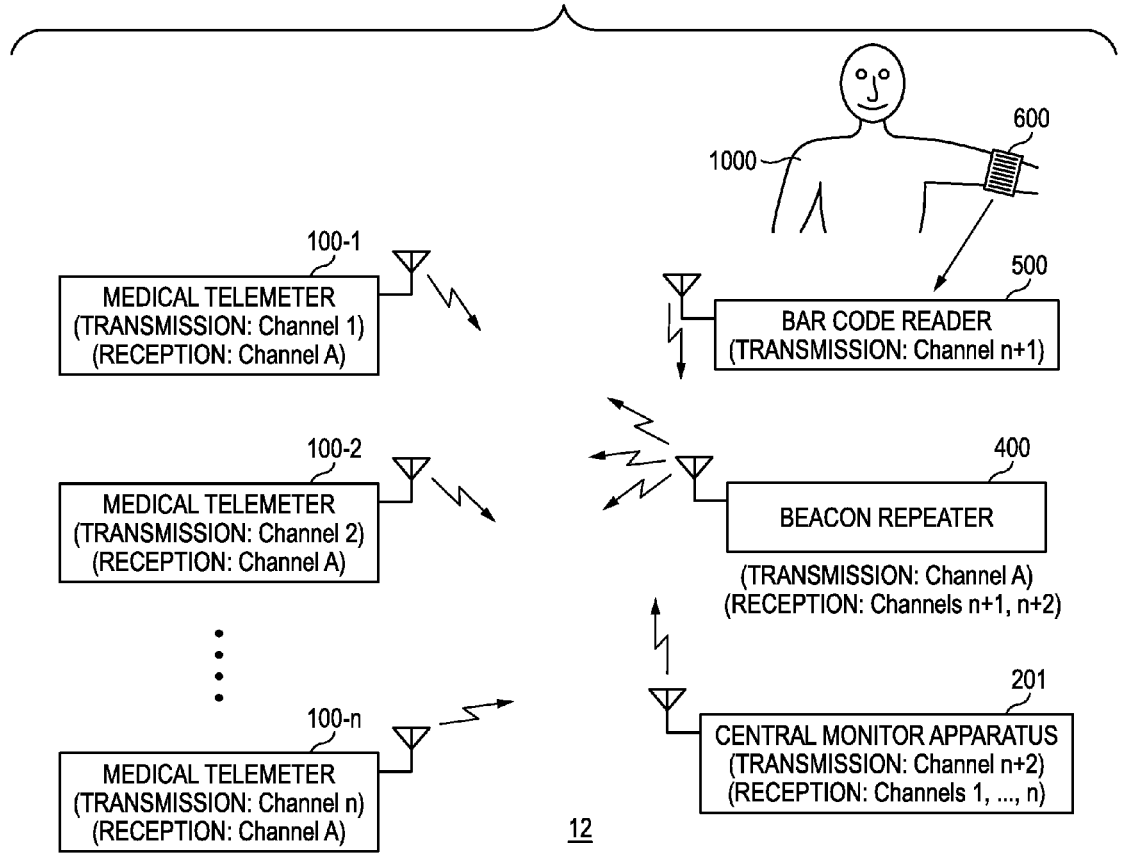
FIG. 5 is a schematic diagram of a medical telemetry system of a third embodiment of the invention.

FIG. 5 is a schematic diagram of a medical telemetry system 12 of a third embodiment of the invention. The medical telemetry system 12 of the embodiment is different from the above-described medical telemetry system 11 in that the system includes a bar code reader 500 which can read a bar code stamped on an arm band 600 attached to an arm of a patient 1000, in place of the external medical apparatus.

The bar code stamped on the arm band 600 is an example of the patient information storage portion in the invention, and indicates, for example, patient information for identifying the patient 1000 wearing the arm band 600. For example, the patient information is an ID allocated to the patient 1000, and the name and birth date of the patient 1000. The patient information is not particularly limited as far as the information identifies the patient 1000. The bar code may further indicate the identification code identifying the medical telemeter 100-X in which the patient information of the patient 1000 is to be registered, in addition to the patient information.

The bar code reader 500 is an example of the patient information acquiring portion in the invention, and a terminal which, when the bar code stamped on the arm band 600 attached to the arm of the patient 1000 is held over the bar code reader, can read the patient information indicated by the bar code. The patient information storage portion is not limited to the above-described bar code, and may be, for example, a medical card incorporating a magnetic stripe or IC chip in which the patient information is written. In this case, for example, a card reader which can read the patient information written in the medical card is used in place of the bar code reader 500 in the embodiment.

The bar code reader 500 includes, in addition to a reading mechanism (not shown) which can read the bar code, at least a communicating portion (not shown) which can transmit the patient information and identification code acquired by reading the bar code, through a predetermined transmission channel to the beacon repeater 400. The identification code may be previously set in a storage portion (not shown) disposed in the bar code reader 500. In place of the above, as described later, the identification code may be previously stored in the beacon repeater 400 which can relay a signal from the bar code reader 500 to a specific medical telemeter 100.

The transmission channel which is used in the transmission of the patient information and the identification code from the bar code reader 500 to the beacon repeater 400 uses a frequency (in the embodiment, "Channel n+1") which is different from, for example, transmission frequencies of the transmission channels (Channel 1, Channel 2, . . . , Channel n) set in the plurality of medical telemeters 100-1, 100-2, . . . , 100-n in the medical radio frequency band.

The third embodiment of the invention has shown the example in which the bar code reader 500 and the beacon repeater 400 communicate with each other by wireless. However, the bar code reader 500 is not required to be connected with the beacon repeater 400 by wireless communication, and may be connected therewith by wired communication. Alternatively, the bar code reader 500 and the beacon repeater 400 may be integrally formed. In this case, the beacon repeater 400 is not required to have a reception channel.

The beacon repeater 400 receives a signal which is transmitted from the bar code reader 500, and which includes the identification code and the patient information, and transmits the first signal including the identification code and the patient information, to the medical telemeter 100. The transmission channel of the beacon repeater 400 in the embodiment is set to Channel A which is identical with that of the beacon repeater 400 included in the medical telemetry system 11, or the frequency in the specified low power radio frequency band. The read information is transmitted to the transmitter, and the transmitter transmits the transmitted information as the first signal to the medical telemeters.

The first signal which is transmitted from the beacon repeater 400 is received by the plurality of medical telemeters 100. Among the plurality of medical telemeters 100, the medical telemeter 100-X in which the identification code coincides with that included in the first signal acquires the patient information included in the first signal, and registers the patient information into the telemeter storage portion 150. Then, the medical telemeter 100-X adds the acquired patient information to the second signal, and transmits the resulting second signal to the central monitor 201.

From the medical telemeter 100-X into which the patient information is newly registered, therefore, the central monitor 201 can receive the patient information. In the case where the central monitor 201 manages the patient information registered in the medical telemeters 100, therefore, it is possible to check whether or not the patient information received from the medical telemeter 100-X is that of the patient 1000 that is to be registered into the medical telemeter 100-X. If the patient information received from the medical telemeter 100-X is different from that to be registered into the medical telemeter 100-X, the central monitor 201 issues an alarm indicating that there is a possibility of misidentification of patients.

In the above-described embodiment, the example in which the medical telemeter 100-X registers the patient information included in the first signal transmitted from the beacon repeater 400, into itself has been shown. In the case where patient information is previously registered in the telemeter storage portion 150 of the medical telemeter 100-X, the medical telemeter 100-X determines whether the acquired patient information coincides with the registered patient information or not. If the acquired patient information does not coincide with the registered patient information, the medical telemeter 100-X issues an alarm indicating that there is a possibility of misidentification of patients. The means for informing that the acquired patient information does not coincide with the registered patient information is not limited to the above-described issuance of an alarm. For example, alarm information may be included in the second signal, and then the second signal is transmitted to the central monitor 201. According to the configuration, the central monitor 201 can rapidly know the medical telemeter 100 in which registered patient information is to be rewritten to different patient information. Therefore, the configuration has a large effect of safety management.

Although the invention has been described using the embodiments, the technical scope of the invention is not restricted to the scope of the description of the embodiments. It is obvious to those skilled in the art that various changes or improvements can be made on the embodiments.

According to an aspect of the invention, it is possible to remotely cause a specific medical telemeter to perform a predetermined operation, and therefore the working efficiency of a medical person is improved.

According to an aspect of the invention, simply by ensuring at least one channel in addition to a frequency (channel) which is required for transmitting a biological signal from the medical telemeter, various operations can be remotely caused to be performed while selecting only the medical telemeter for a specific patient. For example, a medical telemeter which is carried by a specific patient is caused to output an alarm to page the patient.

According to an aspect of the invention, the medical telemeter has the function of identifying itself. When the monitor apparatus is to call the medical telemeter, therefore, it is required only to dispose at least one transmission channel. Consequently, it is possible to selectively cause the specific medical telemeter to execute a predetermined operation while using a small number of channels.

According to an aspect of the invention, in response to instructions (transmission of the first signal) from the monitor apparatus, the specific medical telemeter can be caused to make a sound, emit light, or vibrate. Therefore, it is possible to page a patient who carries the medical telemeter. According to the system, moreover, it is possible to check whether a medical telemeter is adequately attached to a desired patient or not. Therefore, the system also has an effect that misidentification of patients can be prevented from occurring.

According to an aspect of the invention, operations of measuring a biological signal by a specific medical telemeter and registering patient information can be remotely performed by the monitor apparatus. Therefore, a medical person is not required to move to the vicinity of the medical telemeter to operate it, and the working efficiency of a medical person can be improved.

According to an aspect of the invention, it is possible to control start/stop of transmission of a biological signal, and hence a biological signal which is to be transmitted from a medical telemeter to the monitor apparatus can be time-divisionally transmitted. In this case, the monitor apparatus can receive biological signals of a plurality of patients through the same transmission channel.

According to an aspect of the invention, biological information measured by an external medical apparatus and the status of the external medical apparatus can be transmitted as the first signal to the medical telemeter through the transmitter, and the medical telemeter which has received the information can transmit the information as the second signal to the monitor apparatus. Therefore, biological signals of a plurality of external medical apparatuses can be centrally managed, and the working efficiency of a medical person can be improved.

According to an aspect of the invention, the medical telemeter can acquire patient information from the patient information acquiring portion, and, in the case where the patient information does not coincide with that which is registered in the medical telemeter or the monitor apparatus, an alarm can be issued. Therefore, a medical person can promptly know misidentification of patients, and the safety management for the patients can be enhanced.

What is claimed is:

1. A medical telemetry system comprising:
   a transmitter configured to transmit a first signal;
   a plurality of medical telemeters including a first medical telemeter and a second medical telemeter distinct from the first medical telemeter, wherein:
   the first medical telemeter is configured to transmit a second signal including biological information of a patient,
   the first medical telemeter is further configured to receive the first signal and to perform an operation corresponding to information included in the first signal; and
   a monitor apparatus configured to receive the second signal, wherein:
   the transmitter is further configured to transmit the first signal, which includes a first identification code for identifying the first medical telemeter, to the plurality of medical telemeters through a same channel at a same time,
   each of the plurality of medical telemeters is further configured to receive the first signal through the same channel and to determine whether an identification code is included in the received first signal or not, and
   in response to the first medical telemeter determining that the first identification code is included in the received first signal, the first medical telemeter performs the operation corresponding to information included in the first signal.

2. The medical telemetry system according to claim 1, wherein the transmitter is further configured to add the first identification code for identifying the first medical telemeter to the first signal, which includes a command indicating the operation to be performed by the first medical telemeter, then to transmit the first signal.

3. The medical telemetry system according to claim 1, wherein
   the transmitter is further configured to transmit the first signal, which includes a command indicating the operation to be performed by the first medical telemeter, and
   the operation includes at least one of: outputting of a sound, outputting of light, vibrating of the first medical telemeter, starting or stopping of measurement of the biological information, starting or stopping of transmission of the second signal, registering of patient information into the first medical telemeter, and checking of the patient information registered in the first medical telemeter.

4. The medical telemetry system according to claim 1, wherein
   the transmitter is a short-range device, and
   the first medical telemeter is a wireless medical telemetry device.

5. The medical telemetry system according to claim 1, wherein
   the monitor apparatus is further configured to transmit the first identification code for identifying the first medical telemeter and a command indicating the operation to be performed by the first medical telemeter to the transmitter, and
   the transmitter is further configured to transmit the first signal, which includes the first identification code and the command that are transmitted by the monitor apparatus.

6. The medical telemetry system according to claim 1 further comprising an external medical apparatus configured to transmit the first identification code for identifying the first medical telemeter and a command indicating the operation to be performed by the first medical telemeter to the transmitter, wherein:
   the transmitter is further configured to transmit the first signal, which includes the first identification code and the command that are transmitted by the external medical apparatus.

7. The medical telemetry system according to claim 6, wherein the command is an operation instruction command for causing the first medical telemeter to transmit the second signal which includes biological information measured by the external medical apparatus or an alarm issued by the external medical apparatus, wherein
   the biological information or the alarm has been transmitted from the external medical device to the first medical telemeter.

8. The medical telemetry system according to claim 1 further comprising an external medical apparatus configured to transmit a command indicating the operation to be performed by the first medical telemeter to the transmitter, wherein:

the transmitter has the first identification code for identifying the first medical telemeter, and is further configured to transmit the first signal, which includes the first identification code and the command that is transmitted by the external medical apparatus.

9. The medical telemetry system according to claim 8, wherein the command is an operation instruction command for causing the first medical telemeter to transmit the second signal which includes biological information measured by the external medical apparatus or an alarm issued by the external medical apparatus, wherein the biological information or the alarm has been transmitted from the external medical device to the first medical telemeter.

10. The medical telemetry system according to claim 1 further comprising an antenna configured to receive the second signal, wherein the transmitter and the antenna are integrally provided.

11. The medical telemetry system according to claim 1, wherein the transmitter is provided in the monitor apparatus.

12. The medical telemetry system according to claim 1 further comprising:

a patient information storage portion configured to store patient information for identifying a patient; and a patient information acquiring portion configured to acquire the patient information from the patient information storage portion, wherein the patient information acquiring portion is further configured to transmit the first identification code for identifying the first medical telemeter and the acquired patient information, to the transmitter, and the transmitter is further configured to transmit the first signal, which includes the first identification code that is transmitted by the patient information acquiring portion and a command.

13. The medical telemetry system according to claim 12, wherein the first medical telemeter is configured to issue an alarm, in response to an indication that the patient information included in the received first signal does not coincide with patient information registered in the first medical telemeter.

14. The medical telemetry system according to claim 12, wherein the first medical telemeter is further configured to transmit the second signal, which includes the patient information that is included in the received first signal, to the monitor apparatus, and the monitor apparatus is further configured to issue an alarm, in response to an indication that the patient information included in the received second signal does not coincide with patient information registered in the monitor apparatus.

15. The medical telemetry system according to claim 12, wherein the first medical telemeter is further configured to transmit the second signal, which includes the patient information that is included in the received first signal, to the monitor apparatus, and the monitor apparatus is further configured to transmit a command for issuing an alarm to the transmitter, in response to an indication that the patient information included in the received second signal does not coincide with patient information registered in the monitor apparatus.

16. The medical telemetry system according to claim 1 further comprising:

a patient information storage portion configured to store patient information for identifying a patient; and a patient information acquiring portion configured to acquire the patient information from the patient information storage portion, wherein the patient information acquiring portion is further configured to transmit the acquired patient information to the transmitter, and the transmitter has the first identification code for identifying the first medical telemeter and is further configured to transmit the first signal, which includes the first identification code and the patient information that is transmitted by the patient information acquiring portion.

17. The medical telemetry system according to claim 1, wherein the same channel is a same transmission frequency.

18. The medical telemetry system according to claim 1, wherein each of the plurality of medical telemeters is further configured to transmit respective signals including biological information of said patient or other patients at transmission frequencies different than that of the same channel on which the first signal is transmitted and selected from a band ranging from 420 to 450 MHz, and each of the transmission frequencies is respective to respective ones of the medical telemeters such that each medical telemeter transmits at a different frequency within the band ranging from 420 to 450 MHz.

19. The medical telemetry system according to claim 1, wherein the transmitter is further configured to transmit the first signal to the plurality of medical telemeters through the same channel at the same time on a band ranging from 312.5 to 314.5 MHz.

20. The medical telemetry system according to claim 1, wherein each of the plurality of medical telemeters is further configured to receive the first signal through the same channel and through an antenna switchable between a band of low power radio communication, at an antenna power of 250 μW, and a band of weak radio communication, at an antenna power of 500 μV/m.

21. A medical telemeter comprising:

a measuring function, adapted to be attached to a patient, of measuring biological information of the patient;

a receiving function of receiving a signal which is transmitted by a transmitter to a plurality of medical telemeters through a same channel at a same time and which includes an identification code for identifying a medical telemeter;

a transmitting function of transmitting the biological information to an antenna; and an ID determining function of determining whether the received signal includes the identification code for identifying the medical telemeter or not, wherein the medical telemeter is configured to perform an operation, in response to an indication that the ID determining function determines that the identification code for identifying the medical telemeter is included in the signal.

* * * * *